United States Patent
Wild (10) Patent No.: US 11,452,593 B2
(45) Date of Patent: Sep. 27, 2022

(54) METHOD FOR THE MANUFACTURE OF A BREAST PROSTHESIS

(71) Applicant: Amoena Medizin-Orthopädie-Technik GmbH, Raubling (DE)

(72) Inventor: Helmut Wild, Stephanskirchen (DE)

(73) Assignee: Amoena Medizin-Orthopädie-Technik GmbH, Raubling (DE)

( * ) Notice: Subject to any disclaimer, the term of this patent is extended or adjusted under 35 U.S.C. 154(b) by 75 days.

(21) Appl. No.: 16/995,463

(22) Filed: Aug. 17, 2020

(65) Prior Publication Data
US 2022/0047379 A1  Feb. 17, 2022

(51) Int. Cl.
| A61F 2/12 | (2006.01) |
| B29C 65/02 | (2006.01) |
| B29C 65/00 | (2006.01) |
| B29C 70/78 | (2006.01) |
| B29L 31/00 | (2006.01) |

(52) U.S. Cl.
CPC ............... *A61F 2/12* (2013.01); *B29C 65/02* (2013.01); *B29C 66/4326* (2013.01); *B29C 70/78* (2013.01); *A61F 2240/001* (2013.01); *B29L 2031/7532* (2013.01)

(58) Field of Classification Search
CPC ...... A61F 2/12; A61F 2240/001; B29C 65/02; B29L 31/7532
USPC ........................................................ 623/7–8
See application file for complete search history.

(56) References Cited

U.S. PATENT DOCUMENTS

| 4,992,312 | A | * | 2/1991 | Frisch | ...................... C08J 7/043 428/35.7 |
| 8,784,486 | B2 | * | 7/2014 | Schuessler | ................ A61F 2/12 623/8 |
| 2004/0030384 | A1 | * | 2/2004 | Wissman | ............ B29C 65/1435 623/11.11 |
| 2006/0025859 | A1 | * | 2/2006 | Stelter | ...................... A61F 2/52 623/7 |
| 2009/0270985 | A1 | * | 10/2009 | Schuessler | ............ A61F 5/0036 623/8 |
| 2012/0078366 | A1 | * | 3/2012 | Jones | ..................... A61B 90/02 623/8 |
| 2013/0091805 | A1 | * | 4/2013 | Winn | .................... B65B 55/027 53/425 |
| 2013/0131800 | A1 | * | 5/2013 | Schuessler | ................ A61F 2/12 623/8 |

(Continued)

FOREIGN PATENT DOCUMENTS

KR 20080095023 A * 10/2008 ............... A61F 2/12

*Primary Examiner* — Suzette J Gherbi
(74) *Attorney, Agent, or Firm* — McCoy Russell LLP (57) ABSTRACT

The invention relates to a method for the manufacture of a breast prosthesis, comprising: providing and superimposing inner and outer plastic foils; welding together the plastic foils to form the circumferential welding seam, thereby leaving a gap to form a filling channel connecting the inner space to an outside; filling the inner space with a fluid curable mass, which is a precursor of the filler material, by injecting the fluid curable mass into the inner space through the filling channel; and curing the fluid curable mass inside the inner space to form the filler material; wherein the filling channel is provided with a check valve to prevent fluid curable mass from entering the filling channel after injection. The invention additionally proposes a breast prosthesis made by such method.

13 Claims, 9 Drawing Sheets

(56) References Cited

U.S. PATENT DOCUMENTS

| | | | |
|---|---|---|---|
| 2016/0287380 A1* | 10/2016 | Shi | A61F 9/0017 |
| 2018/0186938 A1* | 7/2018 | Ou | A61M 5/2448 |
| 2019/0021881 A1* | 1/2019 | Stelter | A61F 2/52 |
| 2019/0336272 A1* | 11/2019 | Nieto | A61F 2/12 |
| 2020/0276006 A1* | 9/2020 | Felix | A61F 2/52 |
| 2021/0346178 A1* | 11/2021 | Stelter | A61F 2/52 |

* cited by examiner

METHOD FOR THE MANUFACTURE OF A BREAST PROSTHESIS

FIELD OF THE INVENTION

The invention relates to a method for the manufacture of a breast prosthesis. The invention further relates to a breast prosthesis made by such process.

BACKGROUND

Breast prostheses usually comprise shells formed from plastic foils that are welded together along their common circumference. The shells are filled with a material having haptic properties that resemble those of a human breast. Cured silicone polymer materials are most commonly used. During manufacture, a curable liquid silicone material is typically injected into the shell through a filling channel and then thermally cured inside the shell.

The filling channel must be sealed at some point after the injection to avoid a bleeding out of any silicone material. In the state of the art, methods have been developed to seal the filling channel by thermal or ultrasonic welding directly after the injection and still before thermal curing of the silicone mass. Other methods involve local application of a pressure with a heated plunger during the thermal curing process to weld and seal the filling channel. There have also been attempts to seal the channel after the curing process, but this has proven potentially problematic due to residual silicone material inside the filling channel.

The invention aims to provide a further method for the manufacture of a breast prosthesis with emphasis in improving the process of sealing the filling channel in terms of ease and safety.

SUMMARY

Against the background described above, the invention proposes a method for the manufacture of a breast prosthesis, the breast prosthesis comprising a shell, the shell comprising inner and outer plastic foils that are welded together along a common circumference to form a circumferential welding seam and define an inner space of the shell, the inner space being filled with a filler material having haptic properties that resemble those of a human breast; the method comprising: providing and superimposing inner and outer plastic foils; welding together the plastic foils to form the circumferential welding seam, thereby leaving a gap to form a filling channel connecting the inner space to an outside; filling the inner space with a fluid curable mass, which is a precursor of the filler material, by injecting the fluid curable mass into the inner space through the filling channel; and curing the fluid curable mass inside the inner space to form the filler material; wherein the filling channel is provided with a check valve to prevent fluid curable mass from entering the filling channel after injection.

In embodiments of the invention, the check valve is a flapper valve. The check valve may be formed from a pair of plastic foil pieces that are attached to the inner and outer plastic foils, respectively, and protrude into the inner space from the filling channel. The plastic foil pieces may be strip-shaped.

In further embodiments of the invention, the curing may be a thermal curing that is effected by the application of heat to the curable fluid mass.

In yet further embodiments of the invention the filling channel is sealed during curing the fluid curable mass inside the inner space.

A support tube may be inserted into the filling channel prior the injecting of the fluid curable mass and the fluid curable mass may be injected into the inner space through the support tube. In some embodiments, the assembly prior filling is oriented such that the filling channel is positioned at the bottom end of the inner space and the fluid curable mass is injected from below.

In some embodiment the method further comprises a step of venting air from the inner space after the fluid curable mass is injected into the inner space and prior sealing the filling channel and curing the fluid curable mass inside the inner space. The venting may include inserting a venting pipe tube through the filling channel and sucking off air through the venting pipe through a vacuum pump. Especially when the filling channel is positioned at the bottom end of the inner space and the fluid curable mass is injected from below, also the venting pipe may be inserted into the inner space from below and pushed upwards until its tip reaches an air pocket which forms at the top end of the inner space.

Against the background described further above, the invention additionally proposes a breast prosthesis made by the method of the invention.

BRIEF DESCRIPTION OF THE DRAWINGS

The above and other features and advantages of the present invention will become more apparent by reference to the following detailed description when considered in conjunction with the accompanying drawings, in which.

DETAILED DESCRIPTION

The invention proposes a method for the manufacture of breast prostheses and breast prostheses made by such method.

Such a breast prosthesis comprises one or more shells that together have a shape and elasticity properties to resemble the shape and elasticity properties of a human, usually female breast as good as possible. Each shell typically comprises a pair of plastic foils that are welded together along a common circumference to form a circumferential welding seam and define an inner space of the shell. The inner space is typically filled with a filler material having haptic properties that resemble those of a human breast. Most commonly used filler materials comprise two-component silicone rubber materials, which are formed from the curing of a curable liquid two-component silicone composition. The liquid composition may be injected to the inner space of the shell during the process of manufacture through an opening or channel that is subsequently sealed.

Figure 1:
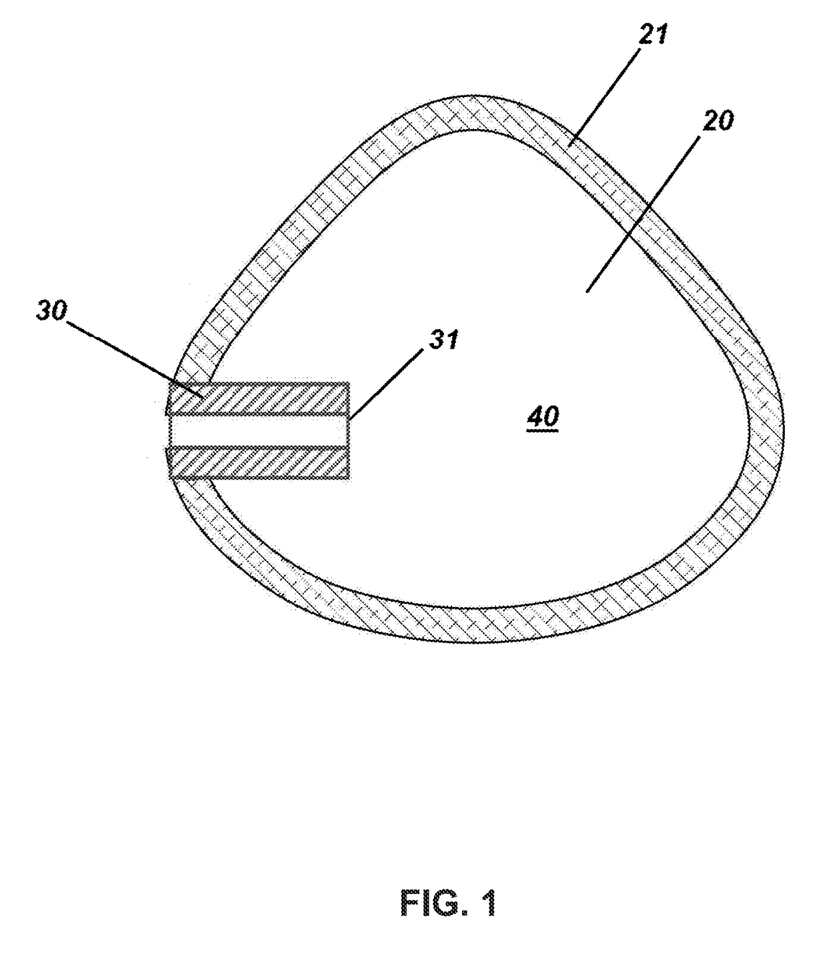
FIG. 1 is a schematic cross-sectional illustration of a breast prosthesis precursor.

The illustration of FIG. 1 shows part of the breast prosthesis to be manufactured, with one lower plastic foil 20 at the bottom and connected to an upper plastic foil, which is not illustrated, by a circumferential welding seam 21. The lower plastic foil 20, the circumferential welding seam 21 and the upper plastic foil follow an approximately triangular shape corresponding to the shape of a female human breast. The plastic foils are made of a thermoplastic polymer material, or at least coated with a thermoplastic polymer material on the surfaces turned towards each other, to enable the forming of the welding seam 21.

A gap in the otherwise continuous welding seal 21 forms a filling channel 30 connecting an outside and the inner space 40 of the breast prosthesis. A pair of congruent strip-shaped plastic foil pieces 31 is welded to the inner and outer plastic foils, respectively, next to the gap. Because the foil pieces 31 are congruent, they appear as one single entity in FIG. 1. The foil pieces 31 protrude into the inner space from the filling channel and form a flapper valve that prevents fluid curable mass from leaking into the filling channel 30 after having been injected into the inner space 40, as described in the following.

Figure 2:
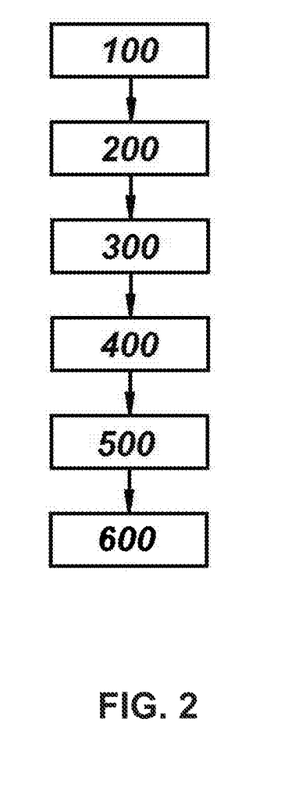
FIG. 2 is a flow diagram of the method according to an embodiment of the invention.

The method of the invention comprises, with reference to the flow diagram of FIG. 2, a first step 100 of providing and superimposing a lower plastic foil 20 and an upper plastic foil and a second step 200 of welding together the plastic foils to form the circumferential welding seam 21. A pair of congruent strip-shaped plastic foil pieces 31 is further provided and included between the plastic foils during step 100. In alternative to being provided separately, the foil pieces 31 may also be already attached to the films. The foil pieces 31 are positioned such as to cover the gap in the welding seam 21.

The filling channel 30 connects the inner space 40 defined between the plastic foils and the welding seam 21 to an outside of the breast prosthesis. The strip-shaped plastic foil pieces 31 that protrude into the inner space 40 form a flapper valve, which enables introduction of a fluid from the outside into the inner space 40 through the filling channel 30, but blocks return movement of a fluid from the inner space 40 into the filling channel 30.

Figure 3:
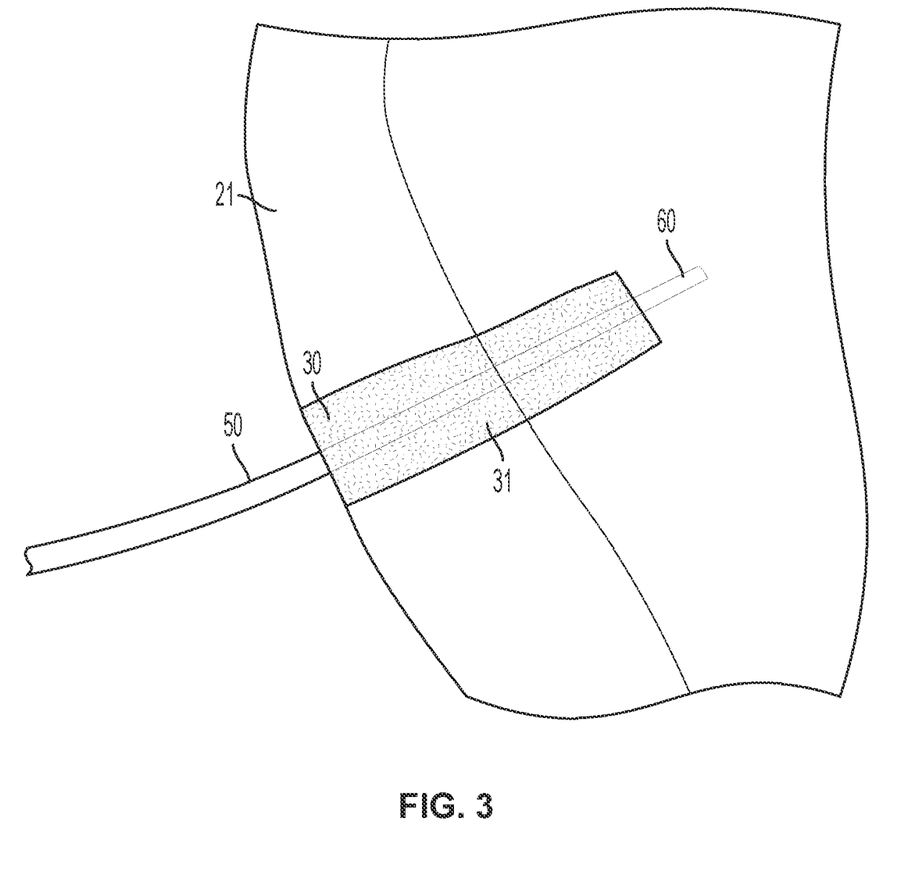
FIG. 3 is a partial photography of a breast prosthesis prior filling, which has a support tube and venting pipe inserted through its filling channel for illustrative purposes.

FIG. 3 shows a photograph of a part of an assembly of welded plastic foils that can be obtained after step 200. It also shows a support tube 50 and a venting pipe 60 inserted into to the filling channel 30 for illustrative purposes.

Figure 4:
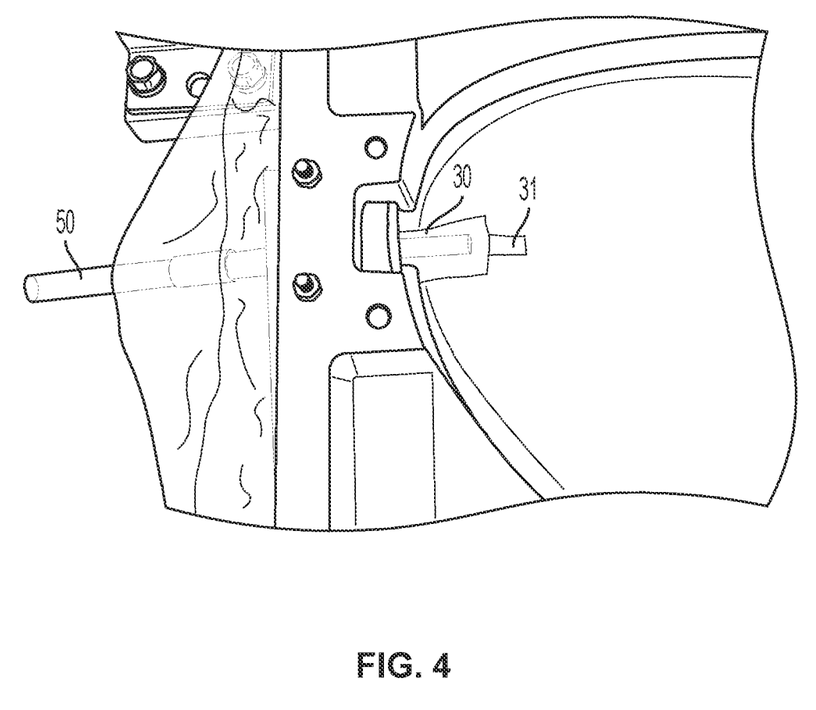
FIG. 4 is a partial photography of a breast prosthesis during support tube insertion.

In a next step 300, that follows the welding step 200, a support tube 50 is inserted into the filling channel, in a manner as shown in FIG. 4, 30 and a silicone filling unit is connected to the support tube 50. The assembly is positioned such that the filling channel 30 is positioned at the bottom of the assembly.

Figure 5A:
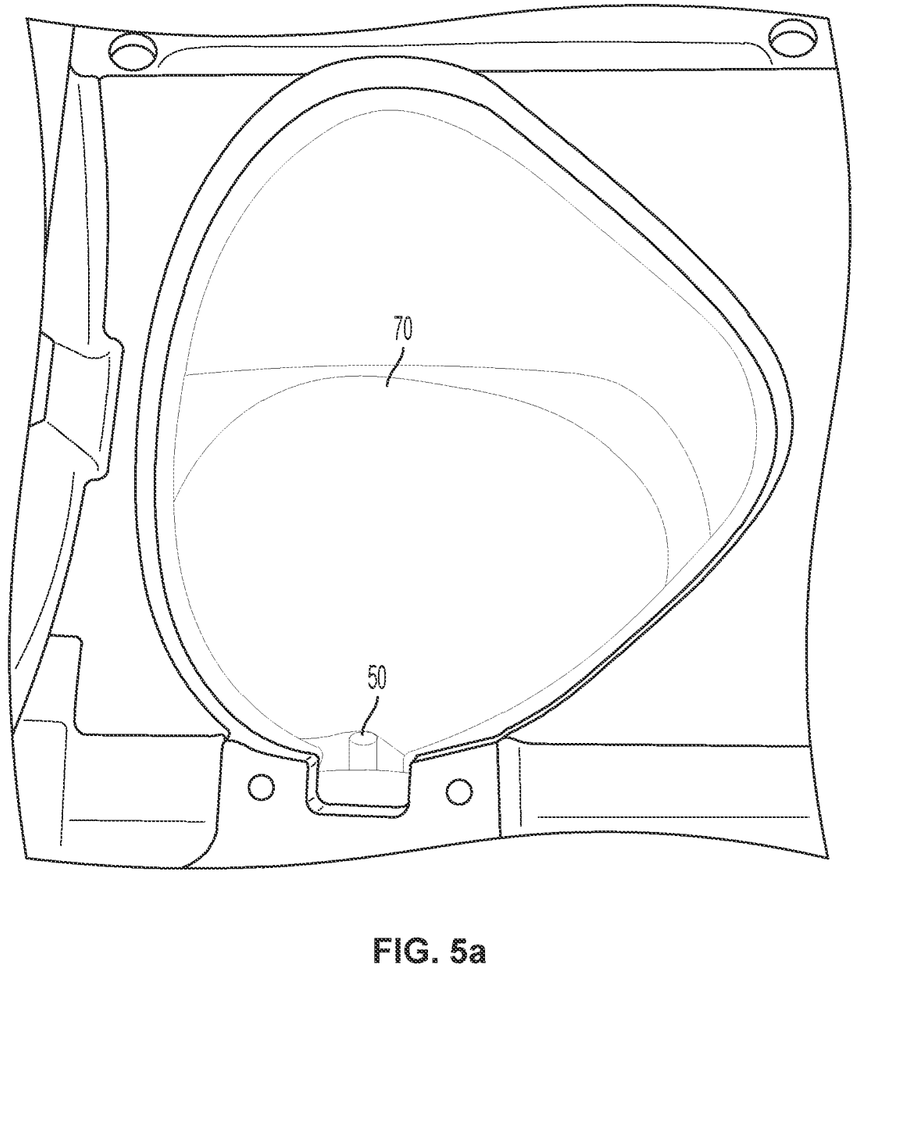
FIGS. 5*a*-5*b* are photographs of the breast prosthesis during filling.
Figure 5B:
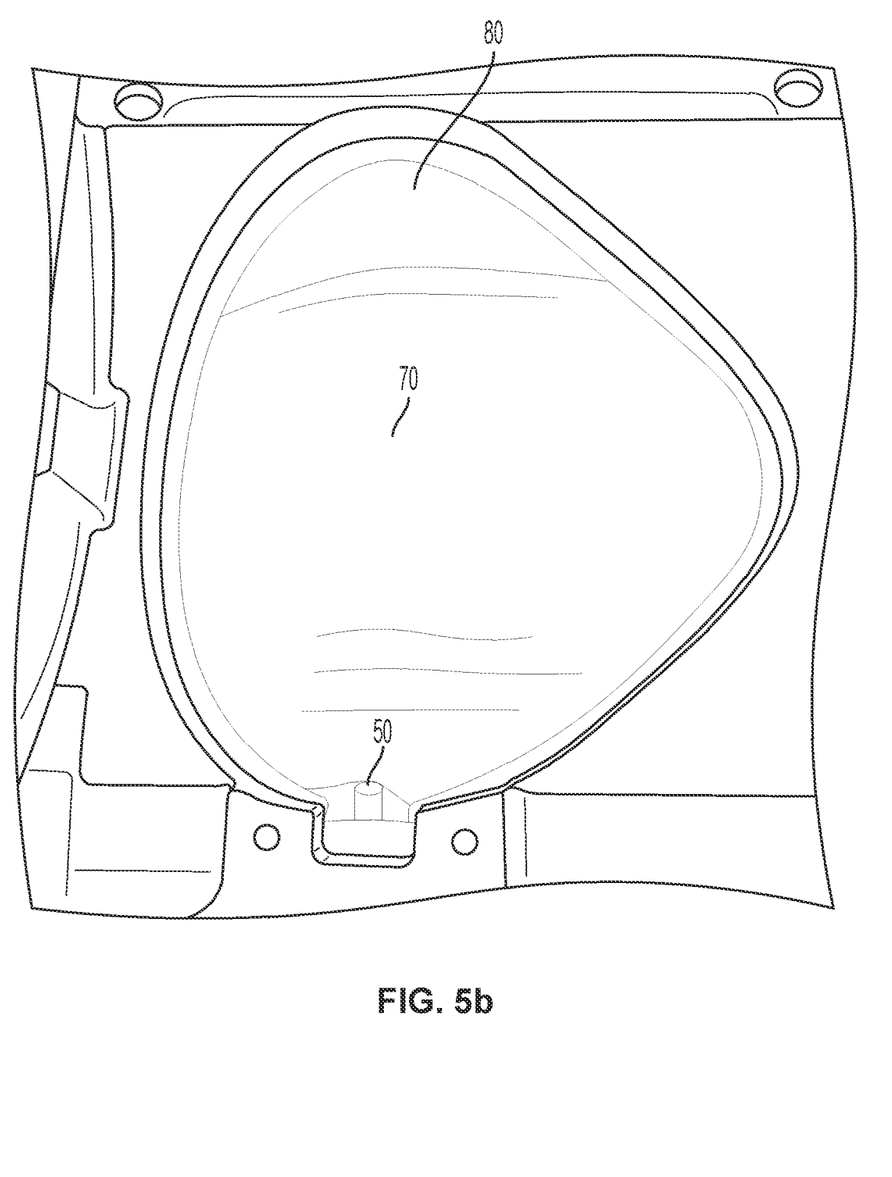

Subsequently, in an injection step 400, in a manner as shown in FIGS. 5a-5b, liquid mass of a curable two-component silicone composition 70 is injected under high pressure through the support tube 50 and hence the filling channel 30 into the inner space 40 until the inner space 40 is filled to a desired extent. Since the filling channel 30 is positioned at the bottom of the assembly, the silicone composition 70 is injected to the inner space 40 from the bottom and an air pocket 80 forms at the top of the inner space 40.

Figure 6A:
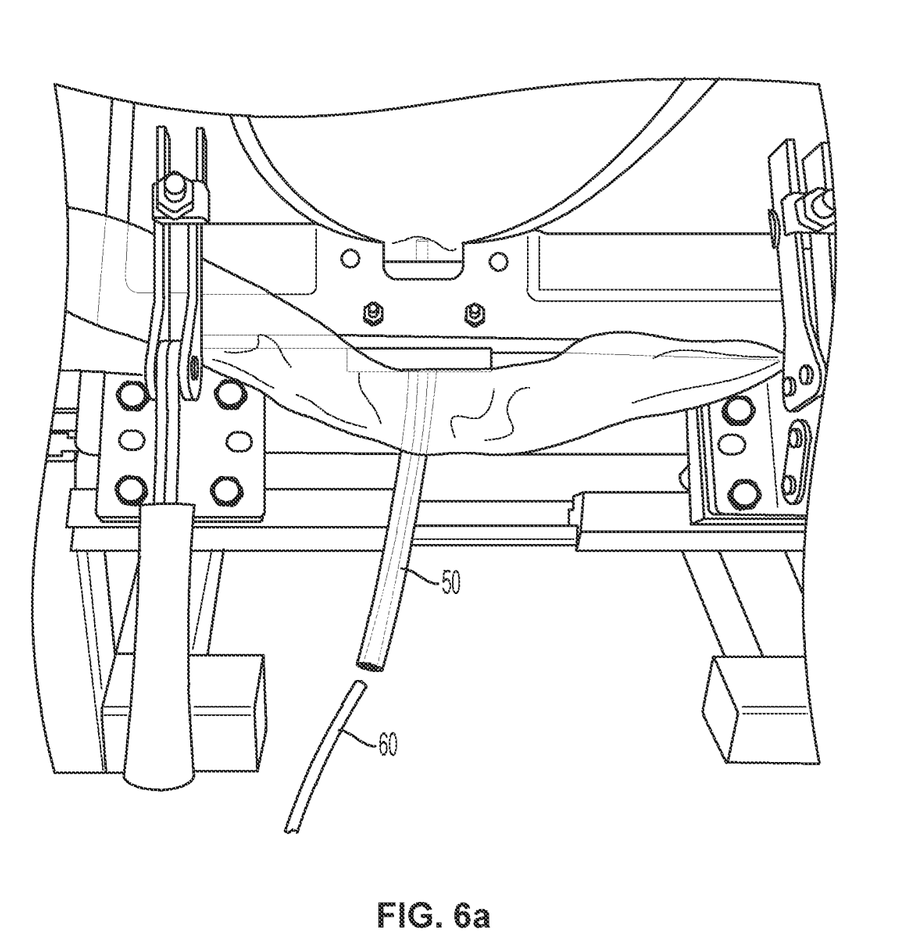
FIGS. 6*a*-6*c* are photographs of the breast prosthesis during venting.
Figure 6B:
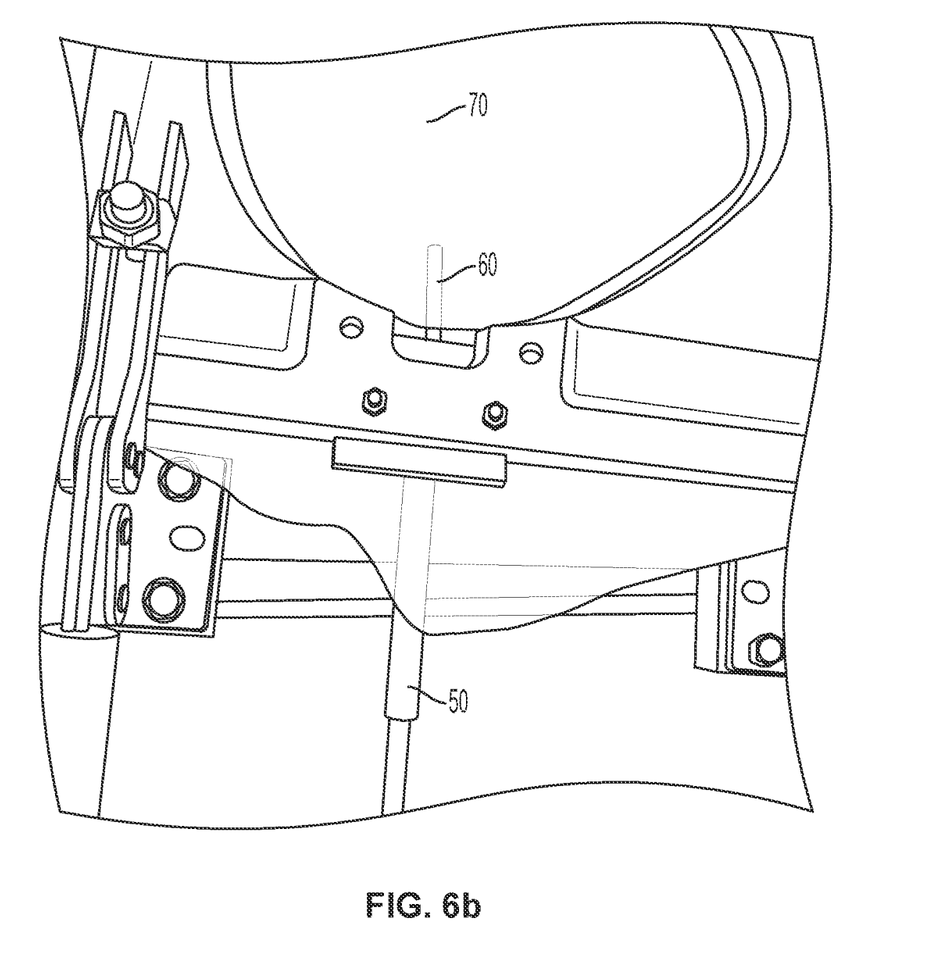
Figure 6C:
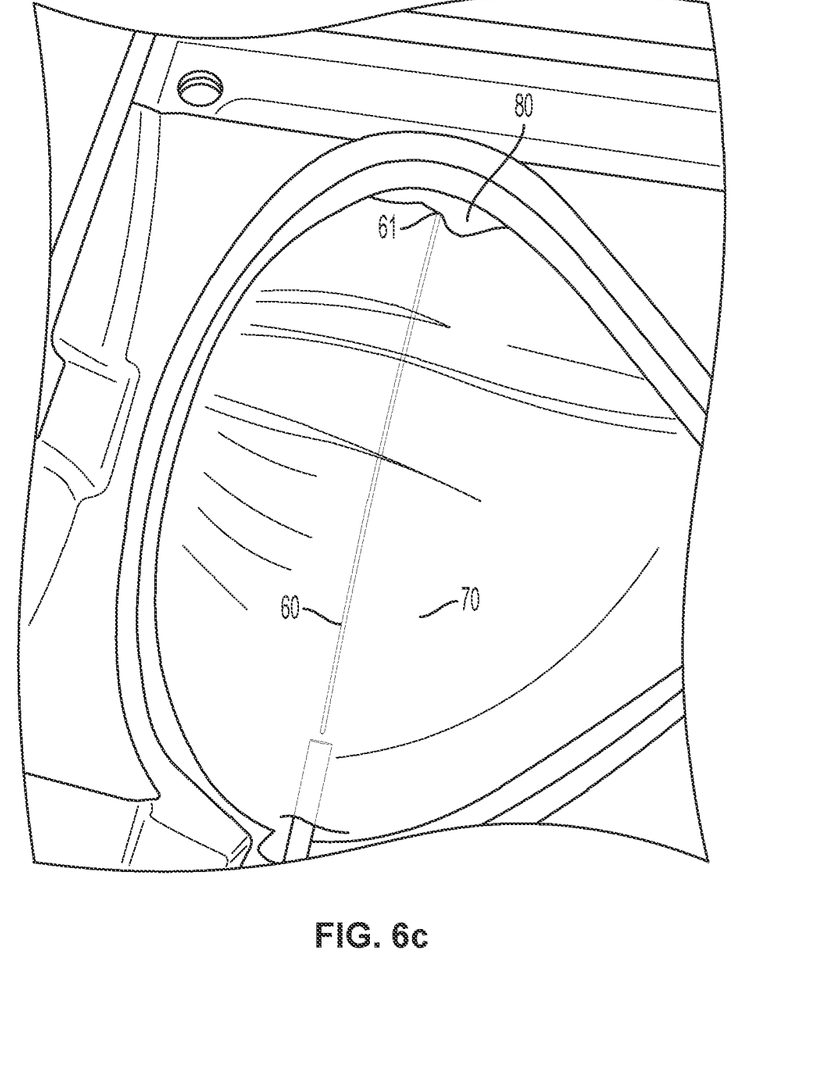

Once the injection is completed, the silicone filling unit is disconnected from the support tube 50 and, in a venting step 500, in a manner as shown in FIGS. 6a-6c, a venting pipe 60 is inserted into the support tube 50 and pushed through the inner space 40 all the way to the top until the tip 61 of the venting pipe 60 reaches the air pocket 80. Air is then sucked off by the action of a vacuum pump that is connected to the venting pipe 60.

After the venting step 500 the support tube 50 and the venting pipe 60 are removed from the filling channel 30 and the flapper valve formed from the strip-shaped plastic foil pieces 31 that protrude into the inner space 40 preliminary seals the inner space 40 such that the liquid mass of silicone composition 70 cannot penetrate the filling channel 30 or even escape to the outside.

The filled shell is then heated in a curing step 600 to effect thermal curing of the curable two-component silicone composition to form an elastic silicone rubber filler material. At the same time, the filling channel 30 may be sealed to close the gap and completely seal the inner space 40. This is not mandatory, however, because even without sealing the necessary leak tightness may be obtained in the inventive embodiments.

A significant advantage over comparable processes of the state of the art, where the filling channel is also sealed during the heat curing of the silicone rubber filling material, is that, due to the presence of the strip-shaped plastic foil pieces 31 that protrude into the inner space 40 and form a flapper valve, no liquid mass cannot penetrate the filling channel or escape to the outside in the time between the finalization of the injection and the thermal curing and sealing of the filling channel. This advantage is emphasized by the problem that any silicone material that penetrates the filling channel negatively interferes with a welding together the tube walls for sealing the filling channel. A heated plunger, that was used in the state of the art to compress the filling channel and complete the welding seam to close the gap and completely seal the inner space, is in some embodiments not any more necessary due to the check valve.

The preceding description has been presented with reference to presently preferred embodiments of the invention. Workers skilled in the art and technology to which this invention pertains will appreciate that alterations and changes in the detailed structure and process steps may be practicable without meaningfully departing from the principal, spirit and scope of this invention. Accordingly, the foregoing description should not be read as pertaining only to the precise embodiments described and illustrated in the accompanying drawings, but rather should be read consistent with and as support for the following claims, which are to have their fullest and fairest scope.

The invention claimed is:

1. A method for the manufacture of a breast prosthesis, the breast prosthesis comprising:
    a shell, the shell comprising inner and outer plastic foils that are welded together along a common circumference to form a circumferential welding seam and define an inner space of the shell, the inner space being filled with a filler material; and the method comprising:
    providing and superimposing inner and outer plastic foils;
    welding together the plastic foils to form the circumferential welding seam, thereby leaving a gap to form a filling channel connecting the inner space to an outside;
    filling the inner space with a fluid curable mass, which is a precursor of the filler material, by injecting the fluid curable mass into the inner space through the filling channel; and
    curing the fluid curable mass inside the inner space to form the filler material;

wherein the filling channel is provided with a check valve to prevent fluid curable mass from entering the filling channel after injection, and wherein the check valve is a flapper valve.

2. The method of claim 1, wherein the check valve is formed from a pair of plastic foil pieces that are attached to the inner and outer plastic foils, respectively, and protrude into the inner space from the filling channel.

3. The method of claim 2, wherein the plastic foil pieces are strip-shaped.

4. The method of claim 1, wherein the curing of the fluid curable mass inside the inner space is a thermal curing and includes the application of applying heat.

5. The method of claim 1, wherein the filling channel is sealed during curing the fluid curable mass inside the inner space.

6. The method of claim 1, wherein the filling channel is sealed by heating and locally applying a pressure for thermal welding.

7. A method for the manufacture of a breast prosthesis, the breast prosthesis comprising:
   a shell, the shell comprising inner and outer plastic foils that are welded together along a common circumference to form a circumferential welding seam and define an inner space of the shell, the inner space being filled with a filler material; and
   the method comprising:
      providing and superimposing inner and outer plastic foils;
      welding together the plastic foils to form the circumferential welding seam, thereby leaving a gap to form a filling channel connecting the inner space to an outside;
      filling the inner space with a fluid curable mass, which is a precursor of the filler material, by injecting the fluid curable mass into the inner space through the filling channel; and
      curing the fluid curable mass inside the inner space to form the filler material:
      wherein the filling channel is provided with a check valve to prevent fluid curable mass from entering the filling channel after injection; and
      wherein a support tube is inserted into the filling channel prior to the injecting of the fluid curable mass and wherein the fluid curable mass is injected into the inner space through the support tube.

8. The method of claim 1, wherein the fluid curable mass is injected from below, with the filling channel being positioned at the bottom end of the inner space.

9. The method of claim 1, further comprising a step of venting air from the inner space after the fluid curable mass is injected into the inner space and prior sealing the filling channel and curing the fluid curable mass inside the inner space.

10. The method of claim 9, wherein the venting includes inserting a venting pipe through the filling channel and sucking off air through the venting pipe through a vacuum pump.

11. The method of claim 10, wherein the venting pipe is inserted into the inner space from below, with the filling channel being positioned at the bottom end of the inner space, and pushed upwards until its tip reaches an air pocket at the top end of the inner space.

12. A breast prosthesis made by the method of claim 2, the breast prosthesis comprising a pair of plastic foil pieces protrudes into the inner space from the welding seam.

13. The breast prosthesis of claim 12, wherein the plastic foil pieces are strip-shaped.

* * * * *